(12) United States Patent
Leinenbach et al.

(10) Patent No.: US 9,314,710 B2
(45) Date of Patent: Apr. 19, 2016

(54) DEVICE FOR THE CHROMATOGRAPHIC SEPARATION OF A SUBSTANCE MIXTURE AND USE THEREOF

(75) Inventors: Hans-Peter Leinenbach, Krems-Rehberg (AT); Franz-Josef Gerner, St. Wendel (DE); Stefan Kuhn, Neunkirchen (DE); Patrick Priesnitz, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 13/881,831

(22) PCT Filed: Oct. 18, 2011

(86) PCT No.: PCT/EP2011/005217
§ 371 (c)(1),
(2), (4) Date: Apr. 26, 2013

(87) PCT Pub. No.: WO2012/055499
PCT Pub. Date: May 3, 2012

(65) Prior Publication Data
US 2013/0220929 A1    Aug. 29, 2013

(30) Foreign Application Priority Data

Oct. 29, 2010 (DE) .................. 10 2010 049 789

(51) Int. Cl.
*B01D 15/22* (2006.01)
*G01N 30/60* (2006.01)
*B01D 15/00* (2006.01)

(52) U.S. Cl.
CPC ............ *B01D 15/22* (2013.01); *G01N 30/6004* (2013.01); *G01N 30/6017* (2013.01); *G01N 30/6091* (2013.01)

(58) Field of Classification Search
None
See application file for complete search history.

(56) References Cited

U.S. PATENT DOCUMENTS

| 4,582,608 A | 4/1986 | Ritacco |
| 4,722,786 A | 2/1988 | Weaver |
| 5,186,826 A | 2/1993 | Otto et al. |

(Continued)

FOREIGN PATENT DOCUMENTS

| CN | 1387037 | 12/2002 |
| CN | 101634646 | 1/2010 |

(Continued)

OTHER PUBLICATIONS

Hostettmann, K., Marston, A., Hostettmann, M. Preparative Chromatography Techniques: Applications in Natural Product Isolation. Springer Science & Business Media, 1998. p. 56.*

(Continued)

*Primary Examiner* — Katherine Zalasky
*Assistant Examiner* — Kara Graber
(74) *Attorney, Agent, or Firm* — Jacobson Holman, PLLC

(57) ABSTRACT

A multifunctional device for chromatographic separation, in particular for affinity chromatographic separation of a substance mixture, provides for a uniform fluid distribution on a separation medium and a uniform flow through a stationary phase. The fluid to be separated is passed through a radial inlet line in an upper partial region of the device, to the center of the upper partial region. The radial inlet line is enlarged in the form of a cupola at the center of the upper partial region.

59 Claims, 2 Drawing Sheets

(56) References Cited

U.S. PATENT DOCUMENTS

| | | | |
|---|---|---|---|
| 5,607,830 | A | 3/1997 | Biesel et al. |
| 6,258,270 | B1 | 7/2001 | Hilgendorff et al. |
| 6,270,674 | B1 | 8/2001 | Baurmeister et al. |
| 2001/0002581 | A1 | 6/2001 | Nishikawa et al. |
| 2004/0084375 | A1* | 5/2004 | Hodgin et al. ............... 210/656 |
| 2004/0089598 | A1 | 5/2004 | Heilmann et al. |
| 2005/0211617 | A1* | 9/2005 | Held et al. ............... 210/198.2 |
| 2005/0242018 | A1* | 11/2005 | Hodgin et al. ............ 210/198.2 |
| 2009/0321338 | A1 | 12/2009 | Natarajan |
| 2011/0262300 | A1 | 10/2011 | Rahn et al. |

FOREIGN PATENT DOCUMENTS

| | | |
|---|---|---|
| DE | 2836007 | 3/1980 |
| DE | 295 05 787 | 7/1995 |
| DE | 19700231 | 10/2001 |
| DE | 102008053131 | 4/2010 |
| EP | 0 106 419 | 4/1984 |
| EP | 0507245 | 10/1992 |
| EP | 0583691 | 3/1997 |
| EP | 0989904 | 9/2002 |
| EP | 1574244 | 9/2005 |
| WO | WO 03/005018 | 1/2003 |

OTHER PUBLICATIONS

Tripathi, Devesh (2002). Practical Guide to Polypropylene. Smithers Rapra Technology. Online version available at: http://app.knovel.com/hotlink/toc/id:kpPGP00002/practical-guide-polypropylene. p. 2.*

Waters Chromatography Columns and Supplies. 2009-2010. www.waters.com.*

Radial. Dictionary.com. Accessed on Dec. 5, 2014 from <http://dictionary.reference.com/browse/radial?s=t>.*

Center. (2011). In the American Heritage dictionary of the English language. Boston, MA: Houhton Mifflin. Retrieved from <http://search.credoreference.com/content/entry/hmdictenglang/center/0.*

* cited by examiner

DEVICE FOR THE CHROMATOGRAPHIC SEPARATION OF A SUBSTANCE MIXTURE AND USE THEREOF

CROSS-REFERENCE TO RELATED APPLICATIONS

This is a national stage of PCT/EP11/005217 filed Oct. 18, 2011 and published in German, which has a priority of German no. 102010049789.4 filed Oct. 29, 2010, hereby incorporated by reference.

BACKGROUND OF THE INVENTION

1. Field of Invention

The invention relates to a device for chromatographic separation of a substance mixture, this device being designed as a housing and containing a separation medium in the central partial area. A radial inlet channel for the fluid to be separated is located in the upper partial area of the device and extends to the center of the upper partial area. The housing has an outlet channel in the lower partial area. Separation elements inside the device serve to delineate the upper and lower partial areas from the separation medium. The structural embodiment of the device according to the invention allows a uniform fluid distribution and essentially simultaneous flow-through of the separation medium.

2. Description of the Prior Art

To achieve a good separation performance with chromatographic separation methods, a uniform distribution of the fluid to be separated on the separation medium as well as a simultaneous flow-through of the separation medium are required. The known devices are used in various areas, for example, in the technical, analytical, medicinal and pharmaceutical fields.

Such chromatographic devices comprise a housing or a column, which is usually subdivided into upper, lower and central partial areas. The separation medium, which is usually in the central partial area, may also be referred to as the stationary phase or the adsorbent. The stationary phase usually comprises a solid, a gel or a substance applied to a carrier.

The medium or fluid to be separated, also known as the mobile phase, flows through the separation medium. The substance mixture comprising the mobile phase may be a liquid and/or may be loaded with solids or suspended matter.

In certain types of applications, the upper and/or lower partial areas have a free space delimiting these areas from the separation medium, the so-called stationary phase. Separation elements comprising screens or meshes are often provided to secure the separation medium in the central partial area. These are often equipped with supporting structures and with special fixtures, which should allow an improved fluid characteristic to improve the stability.

The upper and/or lower partial areas may be closed by an upper and/or lower closure device, which may be embodied as an end cap or end cover.

The inlet and/or outlet of the medium to be separated may thus be both axial and radial.

Numerous chromatographic or adsorptive devices are already known from the state of the art.

EP 0 507 245 B1 describes an adsorber housing having a distributor arrangement, which is embodied in the shape of a funnel and tapers conically toward the center of the housing. Rapid and/or complete sedimentation of the separation medium and an improved separation of the solution to be separated are therefore achieved.

US 2001/002581 A1 describes the design of a filter housing, in which a filter is arranged around a cylindrical tube or in a cylindrical tube. The fluid is introduced and discharged radially, with the inlet tube and the outlet tube being situated at the same height. The drawings show that the separated fluid flows through a bell-shaped space forming a gas space upstream from the outlet tube, thereby provided the venting of the filter system.

EP 1 574 244 A2 discloses an end cap for a filter device having a radial inlet or outlet. Guide elements through which the fluid undergoes a reversal of direction are provided in the end cap. The guide elements are arranged in the area of an essentially circular or partially circular channel.

The patent application WO 03/005018 A1 relates to the optimization of fluid distribution systems, in which the fluid distributor structures used for filter systems are fixedly connected to a mesh for retaining the separation medium. Hygienic problems and the formation of dead volumes should be avoided in this way and an improved flow characteristic of the fluid to be separated should be achieved.

DE 10 2008 053 131 A1 describes a method and an arrangement for sterilizing an adsorber housing and the adsorbent, such that the adsorber housing and the adsorbent to be sterilized are kept separately but form a closed system via a connecting device.

Systems having either small-volume housings or complex larger housings, e.g., made of glass, are used in therapeutic immunopheresis.

One disadvantage of these systems is that they are very expensive and are designed as multiuse applications. In addition, these multiuse systems also entail the risk of contamination due to their repeated used on patients and due to the fact that they must be stored in preservative solutions between individual treatments. Dilution effects occur in systems in which the loaded columns are regenerated repeatedly during treatment, and plasma losses. These disadvantages are always especially critical when:

high regeneration cycles are necessary per treatment and/or larger column volumes are required.

The columns used with disposable systems are not regenerated within one treatment. There is therefore very little or no risk of plasma dilution and/or plasma losses.

Existing disposable systems such as adsorbers that work with amino acid ligands, for example, are suitable only for certain indications because of their low binding capacity and inadequate selectivity.

Larger column volumes must be used with separation media having a low binding capacity. However, larger volumes can be implemented only with larger diameters of the housings at the same time because otherwise the length of the treatment is increased disproportionately.

Although enlarging the housing diameter allows high plasma volume flow rates, distribution problems occur, resulting in the fact that the fluid to be processed enters the separation medium at different times. In these cases, plasma is entrained and therefore unwanted dilution effects occur. This risk increases especially with a column bed having lateral oncoming flow.

However, if columns having a small diameter are used, it is necessary to run higher plasma flow rates. There is the risk that the binding capacity is reduced because in this case the linear flow rate (cm/min) is increased and too little time is available for the intramolecular interaction of the binding partners. In addition, the risk of an excessively high adsorber pressure or column pressure during the rinsing phase is increased because this is performed at much higher volume flow rates.

SUMMARY OF THE INVENTION

The invention is based on the object of making available a multifunctional device for chromatographic separation, in particular for affinity chromatographic separation of a substance mixture, which allows a uniform fluid distribution on the separation column and also permits simultaneous flow through the stationary phase, so that the disadvantages of previous systems can be eliminated in this way. At the same time, the device should have a flat design.

Another object of the invention is to make available such a device which allows use as a disposable item.

In addition, the device should be inexpensive, easy to manufacture and easy and reliable in handling.

This object is achieved according to the invention described herein. The fluid to be separated is guided through a radial inlet line in the upper partial area of the device to its center. At the center of the upper and/or lower partial areas, the inlet line widens in the form of a cupola.

The device according to the invention is suitable for use in the technical, preferably analytical, medical and pharmaceutical fields. Advantageous embodiments of the invention are described herein.

It has surprisingly been found that the fluid distribution on the opposite side of the inflow opening is slowed down due to the cupola-shaped enlargement. The design according to the invention prevents the fluid that is to be separated from striking the housing wall opposite the inflow opening without being decelerated and already penetrating into the separation medium, whereas the fluid to be separated only enters the separation medium with a delay on the side near the inflow. Therefore, this achieves almost simultaneous admission of the fluid to be separated over the entire surface of the separation medium, resulting in an essentially uniform fluid flow through the separation medium.

Due to the cupola-shaped design of the radial inlet at the center of the housing, it is possible to use large-volume separation devices without encountering the negative effects described above.

BRIEF DESCRIPTION OF THE DRAWINGS

The various exemplary embodiments of the invention are explained in greater detail below with reference to the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
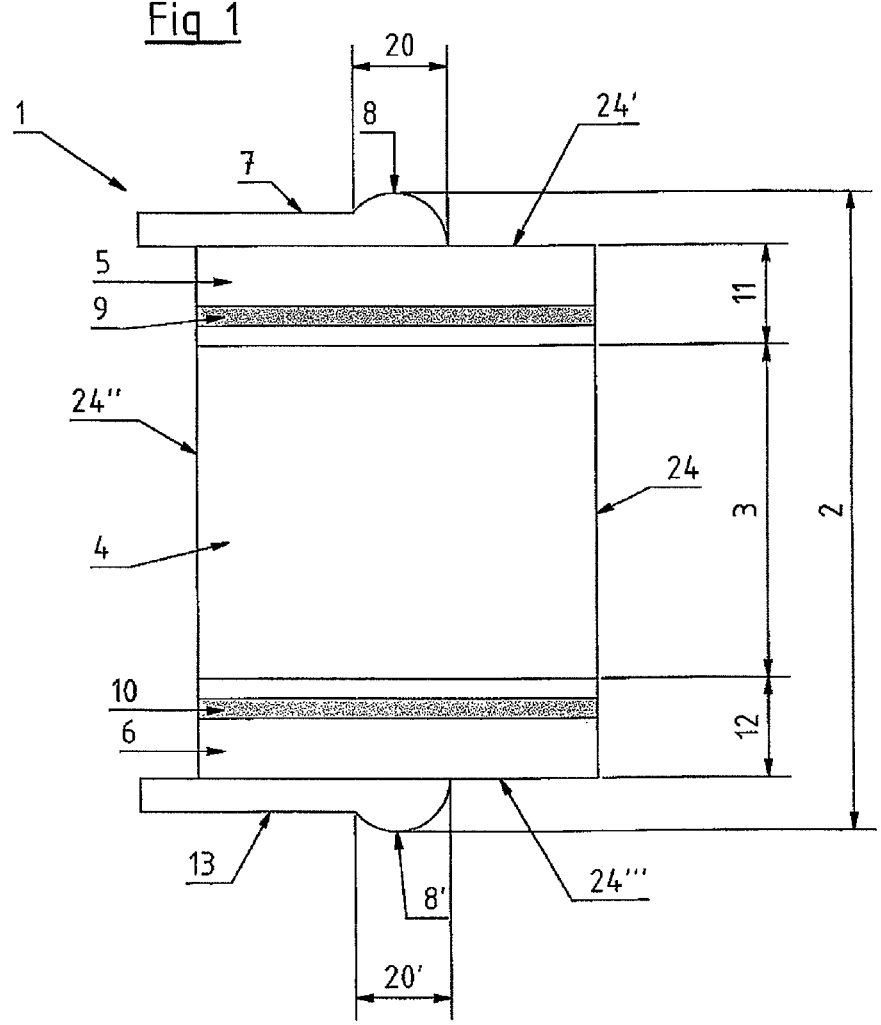
FIG. 1 shows a schematic diagram of the device according to the invention.

As shown in FIG. 1, the device (1) according to the invention comprises a housing (2) having a central partial area (3) containing the separation medium (4), an upper partial area (5) and a lower partial area (6). The upper partial area (5) also has a radial inlet channel (7) extending to the center of the upper partial area (5) and ending in a cupola-shaped enlargement (8). The central partial area (3) is delineated from the upper and lower partial areas (5, 6) by the separation elements (9, 10). A free space (11) and (12) extends from the upper and/or lower partial areas (5, 6) to the separation medium (4). This free space is required, so that the fluid to be separated is distributed to the separation medium (4) and the fluid that has already been separated can run out freely. The device also has an outlet channel (13) in the lower partial area (6). The outlet channel (13) may be embodied in a manner with which those skilled in the art are familiar.

The structural design of the upper partial area (5) in which the radial inlet channel (7) ends in a cupola-shaped enlargement (8) allows a uniform and simultaneous distribution of the fluid to be separated on the inlet surface of the separation medium (4). The traditional systems with radial inflow are often subject to the disadvantage that the fluid to be separated is not distributed simultaneously over the surface of the separation medium. This leads to a nonuniform distribution of the fluid to be separated on the surface of the separation medium and a nonuniform flow of the fluid to be separated through the separation medium. This results in formation of a sloping flow front in the separation medium, leading to the disadvantages described above.

The dimensions of the inlet channel (7), the cupola-shaped enlargement (8) and the inside diameter of the device (1) are directly related and are to be adapted individually to the respective size of the device (1). Thus, in a special embodiment of the device (1), the inside diameter is 3 to 15 cm, preferably 4 to 12 cm, especially preferably 5 to 10 cm.

With the device (1) according to the invention, this yields an inlet area in the range of 7 to 180 $cm^2$ for the separation medium (4), preferably 13 to 115 $cm^2$, especially preferably 20 to 80 $cm^2$, to ensure an optimal separation performance.

The device (1) according to the invention is designed so that the housing (2) is able to hold a separation medium volume of 30 to 1500 mL, preferably 100 to 1000 mL, and is thus also suitable for use for large-volume housings.

The packing height of the separation medium (4) can be calculated on the basis of the sizes given above. However, the packing height is determined mainly by the agent that is to be removed from the fluid to be separated and by the binding capacity of the separation medium (4).

For use in the medical or pharmaceutical fields, the sterility of the device and of the separation medium must be ensured. Sterilization is usually performed by steam sterilization or high-energy ionizing radiation, for example, UV, X-ray, alpha-, gamma- or electron beam radiation, but e-beam radiation is preferred.

In applications in affinity chromatography, proteins, e.g., antibodies, staphylococcal protein A, protein G and the like as well as peptides are often used as carrier-bound ligands. For sterilization of such separation media, only radiation doses in relatively narrowly limited ranges may be used because otherwise the separation media would lose their activity. The separation medium may be inside the housing (endpoint sterilization) or outside the housing in a separate compartment of an irradiation unit. The ability of the entire filled device to be irradiated plays a major role in systems in which endpoint sterilization is provided. Endpoint sterilization is therefore usually considered only in the case of dry separation media and/or those that are stable in sterilization in order to be able to achieve adequate penetration of the radiation. Therefore, it is necessary to find a balance where adequate sterility is ensured while at the same time avoiding any negative effect on the activity of the separation medium. The limiting factor for the radiation dose is thus the separation medium or adsorber material to be sterilized which is to be sterilized and is contained in the housing.

For adequate sterilization, a minimum radiation dose of 25 kGy must be achieved in the entire device 1. This is true of devices, which are subjected to endpoint sterilization as well as devices in which the separation medium is in a separate container. The maximum radiation dose depends on the respective properties of the separation medium used, but the maximum irradiation dose used does not usually exceed approximately 34 kGy.

In an especially preferred embodiment, it is possible due to radial inlet and outlet lines (7, 13) for the fluid to be separated for the outside surfaces (24, 24', 24'', 24''') of the device (1) according to the invention to have a layer thickness greater than 2.5 mm, preferably 1.5 mm. Such a thin housing geometry allows endpoint sterilization with ionizing radiation, even if the separation media are labile in sterilization.

Figure 2:
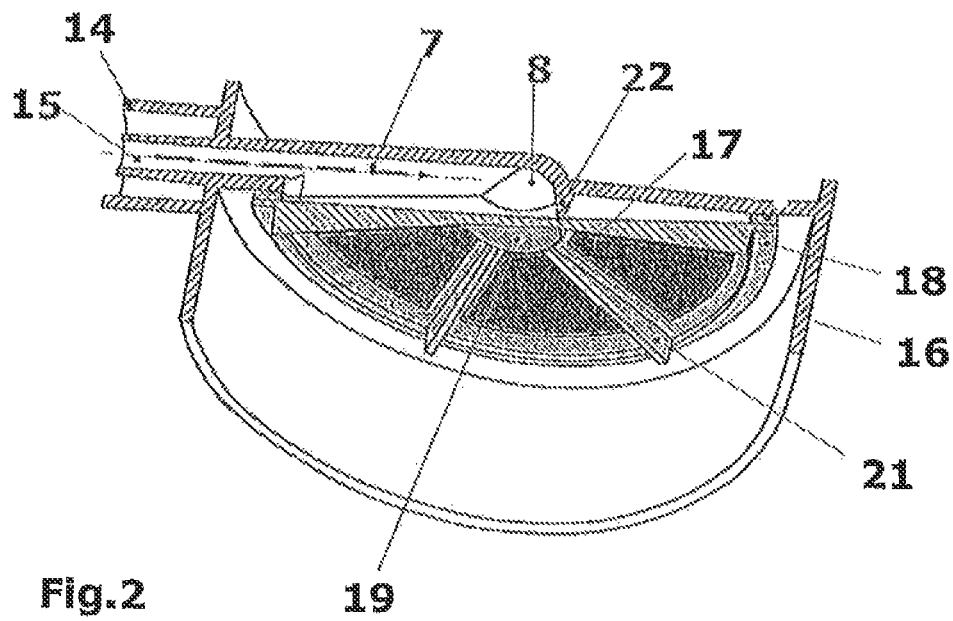
FIG. 2 shows an upper and/or lower partial area of the device according to the invention, including a separation element with a supporting structure.

FIG. 2 illustrates an upper partial region (5) of the device (1) according to the invention, where the radial inlet channel (7) ends in a cupola-shaped enlargement (8) at the center of the device (1). The cupola-shaped enlargement (8) may preferably be designed in the form of a shallow spherical segment. It should be pointed out here that a cupola-shaped enlargement is also understood to include enlargements which may deviate from the circular shape.

In a special embodiment, the inside diameter of the sphere of the cupola-shaped enlargement, preferably an enlargement (8) in the form of a spherical segment may be in the range from 4 to 20 mm, preferably 8 to 16 mm.

In addition, the inlet channel (7), which enlarges in a cupola shape at the center of the upper partial area (5) of the device, preferably in the form of a spherical segment, has a lumen diameter of max. 5 mm, preferably max. 4.2 mm.

Luer or Luer-Lock connections are usually used for connecting the inlet channel to a hose connection. In an especially preferred embodiment, the inlet channel is designed so that it has a conical taper, starting from a standardized Luer or Luer-Lock diameter of the connection side toward the cupola-shaped enlargement, preferably in the form of a spherical segment.

In another preferred embodiment of the device (1) described above, the inlet channel (7) may be open toward the interior of the housing after entering into the interior of the housing to further optimize the uniform and simultaneous distribution of the medium to be separated. The sizes and dimensions defined above may be retained.

In an especially preferred embodiment, a separation element (17) may be provided as an additional structural design of the device (1). The separation element (17) is attached beneath the cupola-shaped enlargement (8), preferably in the form of a spherical segment. Screens, meshes or the like are generally used for such separation elements, serving to affix the separation medium (4) in the central partial region (3) of the housing (2). The screens or meshes used as separation elements (17) are often applied to a supporting structure (18) for sterilization. The separation element (17) may be welded or glued to the supporting structure (18) to form a one-piece unit. In the injection molding process, the supporting structure (18) may be applied to the separation elements (17), which are designed as a screen or mesh.

The supporting structure (18) may be made of polycarbonate (PC), polyethylene (PE), polypropylene (PP), polystyrene (PS), polyvinyl chloride (PVC), polyethylene terephthalate (PET), polybutylene terephthalate (PBT), acrylonitrile-butadiene-styrene (ABS), polyamide (PA) and copolyester. This permits simple and inexpensive production of the separation elements (17) including the supporting device (18).

The supporting structure (18) is also characterized in that a distributor element (19), which may also be referred to as a baffle plate and is designed as a closed surface, is situated at the center of the supporting structure (18) as an integral component. The distributor element (19) is opposite the cupola-shaped enlargement (8), preferably in the form of a spherical segment. The central distributor element (19) is impermeable for the fluid, which is to be separated and is flowing down the cupola-shaped enlargement (8), thereby supporting the simultaneous and uniform distribution of the fluid to be separated on the surface of the separation medium (4), thus achieving an almost horizontal flow front in the separation medium (4).

The device (1) is characterized in that
the diameter of the closed, central distributor element (19) may be 10 to 25 mm in size, preferably 16 to 18 mm, and
the inside diameter (20) of the open side of the cupola-shaped enlargement (8), preferably in the form of a spherical segment, may be 4 to 12 mm in size, preferably 6 to 8 mm.

A ratio value can be calculated from the diameters of the closed, central distributor element (19) to the inside diameters (20) of the open side of the cupola-shaped enlargement (8), preferably in the form of a spherical segment.

This yields a ratio in the range of 2.5/1 to 2.1/1, especially preferably from 2.6/1 to 2.3/1, which is derived from
the diameter of the closed, central distributor system (19) and
the inside diameter (20) of the open side of the cupola-shaped enlargement (8), preferably in the form of a spherical segment.

The inside diameter (20) of the open side of the cupola-shaped enlargement (8), preferably in the form of a spherical segment, may be in the range from 0.5/1 to 4/1, especially preferably 1.5/1 to 3.5/1 in relation to the lumen diameter of the inlet channel (7).

The diameter of the supporting device (18) and the inside diameter of the housing (2) are the same in size, so
the diameter of the supporting device (18) and/or the inside diameter of the housing (2) and
the diameter of the closed, central distributor unit (19) yield a ratio of 6.2/1 to 2.5/1, preferably 5.3/1 to 3.1/1, especially preferably 4/1 to 3.5/1.

The central distributor unit (19), as an integral component of the supporting structure (18) with at least two opposing struts (21), preferably four to eight opposing struts (21), may be connected to the edge area of the supporting structure (18).

The struts (21) additionally serve to support the screen, which is usually flexible. However, they may also be used to affix and position the distributor element (19).

The struts (21) may at the same time serve as spacer elements, so that the separation element (17) and/or the supporting structure (18) do/does not rest directly on the separation medium (4). However, spacer elements may also be attached to the outer edge area of the supporting structure (18) in a suitable shape.

To allow unhindered and uniform fluid flow in the upper partial region (5) of the device (1), the separation element (17) and/or the supporting structure (18) should not abut against the lower edge of the cupola-shaped enlargement (8). This may be achieved by attaching spacer elements (22) beneath the cupola-shaped enlargement (8), preferably in the form of a spherical segment. The spacer elements (22), for example, in the form of spikes, are preferably arranged in the periphery around the cupola-shaped enlargement (8), preferably in the form of a spherical segment.

Spacing by the spacer elements (22) can also be achieved by an elevation in the ring-shaped supporting structure (18).

Figure 3:
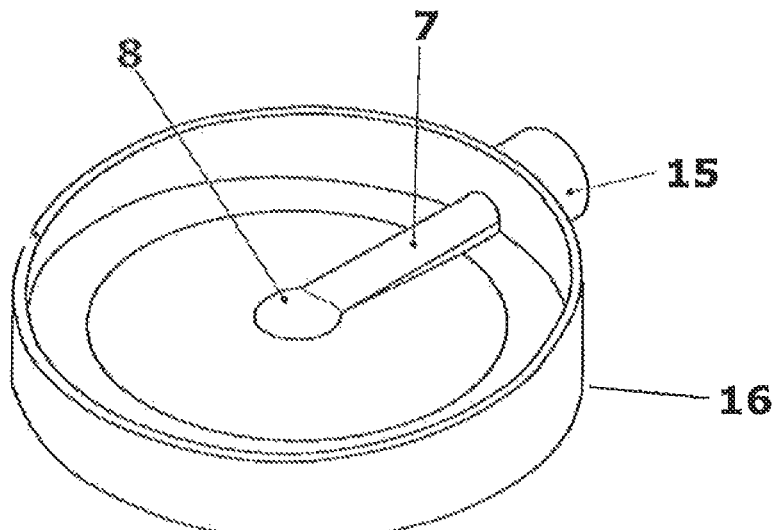
FIG. 3 shows the outer upper partial area of the device according to the invention.

In another preferred embodiment, as shown in FIG. 3, the upper partial region (5) may also be designed as a housing end cap or A housing cover (16). Through the inflow opening (15), the medium to be separated enters the inlet channel (7), which widens in the form of a cupola, preferably in the form of a spherical segment at the center of the housing cover (16). The housing cover (16) may be screwed onto or attached to the central partial section (3) of the housing or otherwise connected to the housing (2). The end of the inlet channel (7) opposite the cupola-shaped enlargement (8) serves to connect a hose line for supplying the medium to be separated and may be designed as a Luer or Luer-Lock connection (14), as shown in FIG. 2. However, the hose line may also be attached directly.

In another preferred embodiment, the outlet or discharge channel (13) for discharging the fluid separated may also be arranged radially according to the inlet channel (7), as shown in FIG. 2.

In an especially preferred embodiment, the outlet channel (13) may extend up to the center of the device (1) and may also develop into a cupola-shaped enlargement (8'), preferably in the shape of a spherical segment, having an inside diameter (20') as shown in FIG. 1.

In a most especially preferred embodiment, the outlet channel (13) has the same features and the same design as well as the same size specifications as those described for the inlet channel (7).

Due to the identical design of the embodiment described above, handling for the user is facilitated and assembly-related operating errors are avoided because the user need not pay attention to a predetermined direction of installation of the device.

To reduce the work sequences in routine use of the device (1) (preservation, storage, rinsing and preparation for reuse) and/or to avoid contamination, it is advantageous to design the device (1) as a disposable item.

The device (1) according to the invention is suitable for use in the technical, preferably analytical, medical and pharmaceutical fields.

The device (1) serves in particular to reduce the concentration of substances from a substance mixture, preferably for reducing the concentration of peptides or proteins, especially preferably cytokines, low-density lipoproteins (LDL), toxic foreign proteins, for example, animal toxins. In addition, the device (1) serves to reduce the concentration of antibodies, which may be endogenous or exogenous antibodies, for example, those having a therapeutic effect. The substances whose concentration is to be reduced may also be of bacterial origin, both Gram-negative and Gram-positive bacteria, for example, endotoxins (lipopolysaccharides) or enterotoxins, for example, toxic shock syndrome toxin-1 (TSST-1) as well as Staphylococcus aureus (SA) and staphylococcal enterotoxin B (SEB).

The reduction in concentration is especially preferably performed starting with whole blood or blood plasma.

The invention is explained in greater detail below on the basis of experimental examples.

Example 1

In a model experiment, a device having a 62 mm inlet diameter of the separation medium was used. This corresponds to an inlet area of the fluid to be separated on the separation medium of approximately 30 $cm^2$. With a height of 47 mm, this yields a separation medium volume of 140 mL. An affinity chromatographic material based on methacrylate was used for the stationary phase.

The mobile phase was passed over a radial inlet channel up to the midpoint of the housing. The radial inlet channel had a lumen diameter of 4.2 mm and was open toward the bottom after the passage into the interior of the housing, widening in the form of a cupola at the center of the housing. The cupola-shaped enlargement had a 17 mm inside spherical diameter. A phenolphthalein solution was used as the mobile phase which would flow through the radial inlet channel at a flow rate of 30 mL/min. The inside diameter of the side of the cupola-shaped enlargement that was open toward the bottom was 7 mm.

The device also had a separation element comprising a supporting structure with a simple distributor element. The diameter of the supporting structure was 59 mm and the diameter of the central distributor plate was 17 mm.

The time was stopped 30 seconds after the start of the inflow of the phenolphthalein solution as the mobile phase, and the distribution of the liquid on the surface of the separation medium was determined at that point in time. It was found that almost 100% of the surface area of the stationary phase was covered at that point in time. In the consideration of the course of the fluid to be separated through the separation medium, an essentially horizontal flow front was found during the separation time.

Example 2

For a comparative experiment, a similar experimental design having the dimensions and materials described above was used, but in this case it was without the cupola-shaped enlargement. The experimental design also had distribution gratings in the cover of the device, which were supposed to ensure a better distribution on the surface of the separation medium. Again in this example, the time was stopped 30 seconds after the onset of the inflow of phenolphthalein solution and the distribution of the liquid on the surface of the separation medium was determined. A significantly inferior liquid distribution above the separation medium along the edge area on the side of the inlet channel was found here. The irregular wetting of the edge area amounted to approximately ⅓ of the separation medium surface.

In comparison with the device according to the invention, it was surprisingly found that in the case of a device having an open channel guide and distributor element but without the cupola-shaped enlargement (see Example 2), an irregular and therefore time-delayed distribution of the fluid to be separated on the separation medium occurred. The distribution gratings in the cover surprisingly did not yield any discernible contribution with regard to a uniform distribution of the fluid to be separated. As a result of the nonuniform distribution over the separation time, the result was a sloping flow front of the fluid to be separated within the separation medium.

With the device according to the invention, an almost uniform and simultaneous distribution of the fluid to be separated on the separation medium was achieved because of the special design of the device. As a result, an essentially horizontal flow front in the separation medium was obtained, so that the disadvantages mentioned initially could be eliminated.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A device for chromatographic separation of a substance mixture, comprising:
    a housing;
    a central partial region containing a separation medium;
    an upper partial region having an inlet channel that extends radially from an outer circumferential edge of the upper partial region to a center point in a middle of an upper plane of the upper partial region;
    a lower partial region having an outlet channel; and
    separation elements, which separate the upper partial region and the lower partial region from the separation medium,
    the inlet channel (i) enlarging in a cupola-shaped enlargement at the center point of the upper plane of the upper partial region and (ii) being open in a direction toward the central partial region from an outer circumferential edge of the upper partial region to the cupola-shaped enlargement.

2. The device according to claim 1, wherein the outlet channel extends radially from an outer circumferential edge of the lower partial region to a center point in a middle of a lower plane of the lower partial region and enlarges in a cupola-shaped enlargement at the center point of the lower plane of the lower partial region.

3. The device according claim 2, wherein the upper partial region with the inlet channel and the cupola-shaped enlargement, and the lower partial region with the outlet channel and the cupola-shaped enlargement, are identical in design.

4. The device according to claim 2, wherein the cupola-shaped enlargement is a shallow spherical segment.

5. The device according to claim 2, further comprising, above the cupola-shaped enlargement of the outlet channel, an outlet separation element.

6. The device according to claim 5, wherein the outlet separation element is a screen element or a mesh element.

7. The device according to claim 5, further comprising an outlet supporting structure having an outlet distributor element that is applied to the outlet separation element.

8. The device according to claim 7, wherein the outlet supporting structure and the outlet separation element are connected in one piece to one another.

9. The device according to claim 7, wherein the outlet supporting structure has a material of construction that is at least one of polyethylene (PE), polypropylene (PP), polystyrene (PS), polyvinyl chloride (PVC), polyethylene terephthalate (PET), polybutylene terephthalate (PBT), acrylonitrile-butadiene-styrene (ABS), polyamide (PA), and a copolyester.

10. The device according to claim 9, wherein the outlet supporting structure has a material of construction that is a polycarbonate (PC).

11. The device according to claim 7, wherein the outlet distributor element has a closed, central surface.

12. The device according to claim 11, wherein a diameter of the outlet supporting structure corresponds to an inside diameter of the housing and forms a ratio of 6.2/1 to 2.5/1 with a diameter of the outlet distributor element having the closed, central surface.

13. The device according to claim 12, wherein the ratio of the inside diameter of the housing and the diameter of the outlet distributor element is from 5.3/1 to 3.1/1.

14. The device according to claim 13, wherein the ratio of the inside diameter of the housing and the diameter of the outlet distributor element is from 4/1 to 3.5/1.

15. The device according to claim 11, wherein a diameter of the outlet distributor element having the closed, central surface is from 10 mm to 25 mm, and an inside diameter of an open side of the cupola-shaped enlargement is from 4 mm to 12 mm.

16. The device according to claim 15, wherein the diameter of the outlet distributor element having the closed, central surface is from 16 mm to 18 mm, and the inside diameter of the open side of the cupola-shaped enlargement is from 6 mm to 8 mm.

17. The device according to claim 15, wherein the diameter of the outlet distributor element having the closed, central surface and the inside diameter of the open side of the cupola-shaped enlargement have a ratio of 2.5/1 to 2.1/1.

18. The device according to claim 17, wherein the diameter of the outlet distributor element having the closed, central surface and the inside diameter of the open side of the cupola-shaped enlargement have a ratio of 2.6/1 to 2.3/1.

19. The device according to claim 1, wherein the cupola-shaped enlargement has a form of a shallow spherical segment.

20. The device according to claim 19, wherein diameters of the shallow spherical segment and at least one of the inlet channel and the outlet channel have a ratio of 0.5/1 to 4/1.

21. The device according to claim 20, wherein the ratio of the diameters of the shallow spherical segment and the at least one of the inlet channel and the outlet channel is from 1.5/1 to 3.5/1.

22. The device according to claim 19, wherein the shallow spherical segment has an inside diameter of 4 mm to 20 mm.

23. The device according to claim 22, wherein the shallow spherical segment has an inside diameter of 8 mm to 16 mm.

24. The device according to claim 1, wherein at least one of the inlet channel and the outlet channel has a maximum lumen diameter of 5 mm.

25. The device according to claim 24, wherein the at least one of the inlet channel and the outlet channel has a maximum lumen diameter of 4.2 mm.

26. The device according to claim 1, wherein the housing has an inside diameter of 3 cm to 15 cm.

27. The device according to claim 26, wherein the inside diameter is from 4 cm to 12 cm.

28. The device according to claim 27, wherein the inside diameter is from 5 cm to 10 cm.

29. The device according to claim 1, wherein the separation medium has an inlet area of 7 $cm^2$ to 180 $cm^2$.

30. The device according to claim 29, wherein the inlet area is from 13 $cm^2$ to 115 $cm^2$.

31. The device according to claim 30, wherein the inlet area is from 20 $cm^2$ to 80 $cm^2$.

32. The device according claim 1, wherein the separation medium has a volume of 30 mL to 1500 mL.

33. The device according claim 32, wherein the volume is from 100 mL to 1000 mL.

34. The device according to claim 1, wherein outside surfaces of the housing have a layer thickness of at least 2.5 mm.

35. The device according to claim 1, wherein the outlet channel is open in a direction toward the central partial region along an entire length of the outlet channel within the housing.

36. The device according to claim 1, further comprising, below the cupola-shaped enlargement of the inlet channel, an inlet separation element.

37. The device according to claim 36, further comprising an inlet supporting structure having an inlet distributor element that is applied to the inlet separation element.

38. The device according to claim 37, wherein the inlet supporting structure and the inlet separation element are connected in one piece to one another.

39. The device according to claim 37, wherein the inlet supporting structure has a material of construction that is at least one of polyethylene (PE), polypropylene (PP), polystyrene (PS), polyvinyl chloride (PVC), polyethylene terephthalate (PET), polybutylene terephthalate (PBT), acrylonitrile-butadiene-styrene (ABS), polyamide (PA), and a copolyester.

40. The device according to claim 39, wherein the inlet supporting structure has a material of construction that is a polycarbonate (PC).

41. The device according to claim 37, wherein the inlet distributor element has a closed, central surface.

42. The device according to claim 41, wherein a diameter of the inlet distributor element having the closed, central surface is from 10 mm to 25 mm, and an inside diameter of an open side of the cupola-shaped enlargement is from 4 mm to 12 mm.

43. The device according to claim 42, wherein the diameter of the inlet distributor element having the closed, central surface and the inside diameter of the open side of the cupola-shaped enlargement have a ratio of 2.5/1 to 2.1/1.

44. The device according to claim 42, wherein the diameter of the inlet distributor element having the closed, central surface is from 16 mm to 18 mm, and the inside diameter of the open side of the cupola-shaped enlargement is from 6 mm to 8 mm.

45. The device according to claim 42, wherein the diameter of the inlet distributor element having the closed, central surface and the inside diameter of the open side of the cupola-shaped enlargement have a ratio of 2.6/1 to 2.3/1.

46. The device according to claim 41, wherein a diameter of the inlet supporting structure corresponds to an inside diameter of the housing and forms a ratio of 6.2/1 to 2.5/1 with a diameter of the inlet distributor element having the closed, central surface.

47. The device according to claim 46, wherein the ratio of the inside diameter of the housing and the diameter of the inlet distributor element is from 5.3/1 to 3.1/1.

48. The device according to claim 47, wherein the ratio of the inside diameter of the housing and the diameter of the inlet distributor element is from 4/1 to 3.5/1.

49. The device according to claim 36, wherein the inlet separation element is a screen element or a mesh element.

50. The device according to claim 1, further comprising spacer elements arranged beneath the cupola-shaped enlargement.

51. The device according to claim 50, wherein the spacer elements are arranged at a periphery around the cupola-shaped enlargement.

52. The device according to claim 1, wherein the device is configured to effect the chromatographic separation in at least one of a technical, an analytical, a medical, and a pharmaceutical field.

53. The device according to claim 52, wherein the device is configured to effect the chromatographic separation to reduce a concentration of substances from the substance mixture.

54. The device according to claim 53, wherein the device is configured to effect the reduction in concentration from whole blood or blood plasma.

55. The device according to claim 53, wherein the concentration reduced is of peptides or proteins.

56. The device according to claim 55, wherein the concentration reduced is of at least one of cytokines, low-density lipoproteins (LDL), toxic foreign proteins, antibodies, endotoxins and enterotoxins.

57. The device according to claim 1, wherein outside surfaces of the housing have a layer thickness of at least 1.5 mm.

58. A device for chromatographic separation of a substance mixture, said device comprising:
   a housing;
   a central partial region containing a separation medium;
   a first partial region having a first channel that extends radially from an outer circumferential edge of the first partial region to a center point in a middle of an upper plane of the first partial region;
   a second partial region having a second channel that extends radially from an outer circumferential edge of the second partial region to a center point in a middle of a lower plane of the second partial region; and
   separation elements, which separate the first partial region and the second partial region from the separation medium,
   the first channel terminating in a first cupola-shaped enlargement at the center point of the upper plane of the first partial region, and the second channel terminating in a second cupola-shaped enlargement at the center point of the lower plane of the second partial region,
   with the first channel being open in a direction toward the central partial region from an outer circumferential edge of the first partial region to the first cupola-shaped enlargement, and the second channel being open in a direction toward the central partial region from an outer circumferential edge of the second partial region to the second cupola-shaped enlargement.

59. The device according to claim 58, wherein the first cupola-shaped enlargement and the second cupola-shaped enlargement are each configured as a shallow spherical segment.

* * * * *